United States Patent
Calderon (10) Patent No.: US 10,853,612 B2
(45) Date of Patent: Dec. 1, 2020

(54) OPTICAL DETECTION OF AN IMAGE ON A CONTAINER

(71) Applicant: Fenwal, Inc., Lake Zurich, IL (US)

(72) Inventor: Carlos Calderon, Waukegan, IL (US)

(73) Assignee: Fenwal, Inc., Lake Zurich, IL (US)

( * ) Notice: Subject to any disclaimer, the term of this patent is extended or adjusted under 35 U.S.C. 154(b) by 50 days.

(21) Appl. No.: 16/401,132

(22) Filed: May 2, 2019

(65) Prior Publication Data

US 2019/0340403 A1 Nov. 7, 2019

Related U.S. Application Data

(60) Provisional application No. 62/666,247, filed on May 3, 2018.

(51) Int. Cl.
| | |
|---|---|
| *G06F 17/00* | (2019.01) |
| *G06K 7/14* | (2006.01) |
| *A61J 1/10* | (2006.01) |
| *A61M 1/02* | (2006.01) |
| *A61M 39/18* | (2006.01) |

(52) U.S. Cl.
CPC .............. *G06K 7/1434* (2013.01); *A61J 1/10* (2013.01); *A61M 1/0209* (2013.01); *A61M 39/18* (2013.01); *A61M 2205/10* (2013.01)

(58) Field of Classification Search
CPC ..... B65D 85/8043; G06K 7/14; G06K 7/1413
USPC ................................. 235/375, 454, 472.01
See application file for complete search history.

(56) References Cited

U.S. PATENT DOCUMENTS

| 4,018,911 A | 4/1977 | Lionetti et al. |
| 7,322,525 B2 * | 1/2008 | Itoh .................. G01N 35/00732 235/462.43 |
| 2003/0074223 A1 | 4/2003 | Hickle et al. |
| 2005/0011202 A1 | 1/2005 | Voute et al. |
| 2010/0291619 A1 | 11/2010 | Robinson et al. |
| 2011/0192745 A1 | 8/2011 | Min |
| 2018/0207595 A1 * | 7/2018 | Bacallao ............. B01F 15/0222 |

FOREIGN PATENT DOCUMENTS

| DE | 10056181 C1 | 3/2002 |
| WO | 1995002425 A1 | 1/1995 |
| WO | WO 2017/048673 A1 | 3/2017 |

OTHER PUBLICATIONS

Partial European Search Report from the European Patent Office for European Application No. 19172158.8, dated Sep. 18, 2019 (13 Pages).

* cited by examiner

*Primary Examiner* — Jamara A Franklin
(74) *Attorney, Agent, or Firm* — Cook Alex Ltd.

(57) ABSTRACT

A container is mounted with respect to a fluid processing device using first and second supports, with the first support engaging a first portion of the container and the second support engaging a second portion of the container. The second support is positioned above or below the first support. The first and second supports cooperate to restrain the container in a fixed orientation, such as aligning an image on the container with an optical detector of a fluid processing device. The first and second supports may be components of a fixture that is separate from a surface of the fluid processing device or may themselves be incorporated into and extend from the surface of the fluid processing device.

21 Claims, 6 Drawing Sheets

OPTICAL DETECTION OF AN IMAGE ON A CONTAINER

CROSS-REFERENCE TO RELATED APPLICATIONS

This application claims the benefit of and priority of U.S. Provisional Patent Application Ser. No. 62/666,247, filed May 3, 2018, the contents of which are incorporated by reference herein.

BACKGROUND

Field of the Disclosure

The present disclosure relates to optical detection of an image on a fluid container. More particularly, the present disclosure relates to apparatus and methods for ensuring optical detection of an image on a fluid container when the fluid container is mounted adjacent to an optical detector.

Description of Related Art

It is well known to optically detect an image on a fluid flow circuit, such as a disposable fluid flow circuit used in processing collected whole blood. For example, for blood processing devices capable of executing different procedures (e.g., a first procedure separating and collecting only red blood cells from blood and a second procedure separating and collecting plasma and red blood cells from blood), differently configured fluid flow circuits may be provided for mounting on the device. Each fluid flow circuit (or a package thereof) may include an image, such as a barcode, that represents the procedure for which the fluid flow circuit is to be used. After selecting the procedure to be executed, but before executing the procedure, an optical detector (e.g., a barcode reader) may be used to detect the image to determine whether a particular fluid flow circuit is suitable for the selected procedure.

PCT Patent Application Publication No. WO 2017/048673 A1, which is hereby incorporated herein by reference, describes a blood processing device including a plurality of optical detectors and a plurality of hangers for hanging different fluid containers of a disposable fluid flow circuit mounted to the device. One of the optical detectors is handheld and movable with respect to the device, with each of the remaining optical detectors being fixedly secured to the device and associated with a different one of the hangers. In use, different fluid containers of the circuit are mounted to the different hangers and oriented such that the associated optical detector may optically detect an image on the fluid container, which may provide the device with information regarding the circuit and/or the fluid container (e.g., whether the fluid container has been hung from the proper hanger).

Proper orientation of a fluid container with respect to the associated optical detector ensures that the optical detector is capable of optically detecting the image on the fluid container. However, the fluid containers are typically formed of a flexible material, meaning that their orientation with respect to the associated optical detector is not strictly controlled or predictable. If a fluid container is at least partially filled with a fluid at the time that it is mounted to the device, then that may cause the fluid container to hang flat with respect to the associated optical detector, which makes it more likely that the optical detector will be able to optically detect an image on the fluid container. However, if the fluid container is empty when it is mounted to the device, it may have a tendency to hang in a manner that is not conducive to optical detection of an image on the fluid container. For example, the fluid container may rotate out of alignment with the optical detector or fail to hang sufficiently vertically so as to position the image in view of the optical detector.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fixture is provided for mounting a container. The fixture includes a frame, a first support, and a second support. The first support extends from a first portion of the frame and is configured to engage a first portion of a container. The second support extends from a second portion of the frame, which is positioned above or below the first portion of the frame, with the second support being configured to engage a second portion of the container. The first and second supports are configured to cooperate to restrain the container in a fixed orientation.

In another aspect, a fluid processing device includes a surface, an optical detector associated with the surface, and first and second supports extending from the surface. One of the first and second supports is positioned above the optical detector, while the other one of the first and second supports is positioned below the optical detector. The first support is configured to engage a first portion of a container including an image positioned between the first portion and a second portion of the container, while the second support is configured to engage the second portion of the container. The first and second supports are configured to cooperate to restrain the container in a fixed orientation with respect to the optical detector.

In yet another aspect, a method is provided for mounting a container to a fluid processing device of the type including an optical detector associated with a surface of the fluid processing device. The method includes providing a container including a first portion, a second portion, and an image positioned between the first and second portions. The first portion of the container is associated to a first support extending from the surface, while the second portion of the container is associated to a second support extending from the surface, with one of the supports being positioned above the optical detector and the other support being positioned below the optical detector. The supports cooperate to restrain the container in a fixed orientation with respect to the optical detector, with the image in at least general alignment with the optical detector.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

A. Fluid Processing System

Figure 1A:
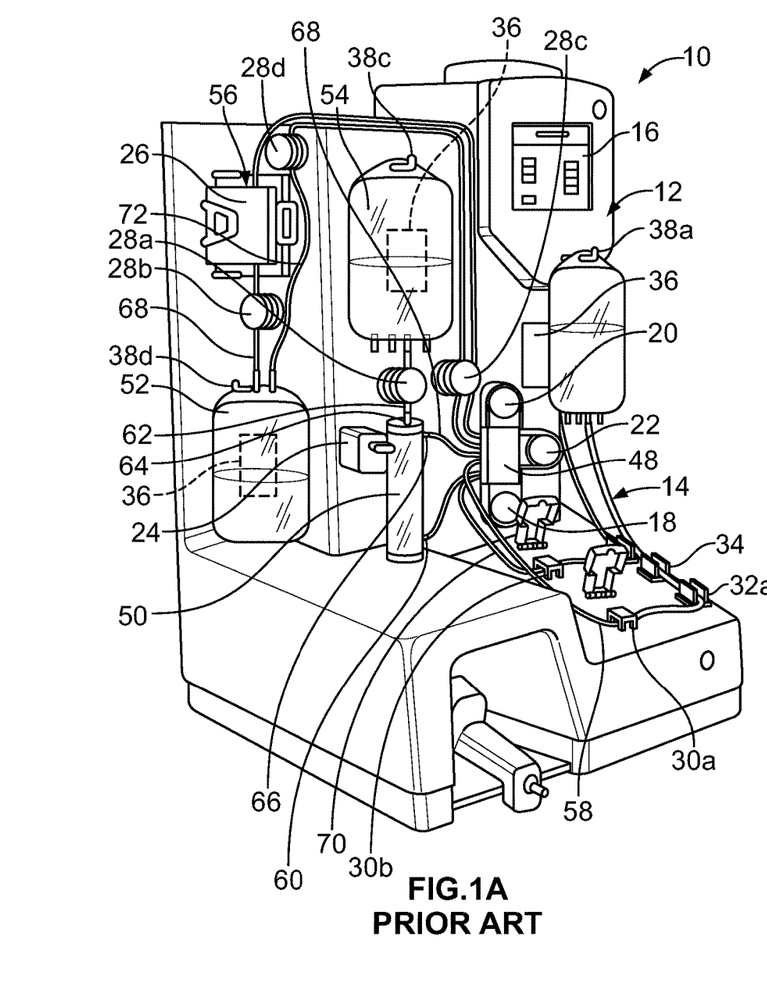
FIG. 1A is a perspective view of a fluid processing system of known configuration, employing a reusable durable portion and a disposable fluid flow circuit formed from a plurality of fluid flow sub-systems or modules.

FIG. 1 depicts an exemplary fluid processing system, generally at 10, which includes a durable, reusable processing device 12 and a disposable fluid flow circuit 14. The illustrated fluid processing system 10 may be particularly useful in processing whole blood and will be described in this context, but it should be understood that the present disclosure is not limited to the processing of a particular fluid. The illustrated fluid processing device 12 includes associated pumps, valves, sensors, displays, and other apparatus for configuring and controlling flow of fluid and additive solution through the disposable circuit 14. The operation of the processing device 12 may be directed by an internal controller that includes a programmable microprocessor automatically controlling the operation of the pumps, valves, sensors, etc.

More specifically, the illustrated processing device 12 includes a user input and output touchscreen 16; a pump station including a fluid pump 18 (which may comprise a whole blood pump when blood is being processed), a fluid component pump 20 (which may be a red blood cell pump), and an additive solution pump 22; a fluid separator mounting station and drive unit 24; filter housing 26 (which may be a leukocyte filter housing); tubing clamp/RF sealer/sensors 28a-28d, sterile connection or docking devices 30a and 30b; tubing clamps 32a and 32b; a sensor 34 (which may be a hematocrit sensor); and container scanners or optical detectors 36. The processing device also includes hangers 38a-38d, each associated with a weight scale, for suspending the various containers of the disposable fluid circuit.

As shown, the fluid flow circuit is provided in three separate modules, each of which is individually pre-assembled, and which are joined together on the processing device. These modules are—(i) an additive solution module that includes a pre-filled additive solution container 40 (FIG. 1B) and associated fluid flow tubing 42 for withdrawing the additive solution, (ii) a fluid module (which may be a whole blood module) that includes at least the fluid container 44 (which may be a whole blood container) and associated fluid flow tubing 46 for withdrawal of collected fluid (which may be whole blood) from the fluid container 44, and (iii) a processing module that includes a pump cassette 48, a membrane separator 50, a first fluid component container 52 (which may be a red blood cell container), a second fluid component container 54 (which may be a plasma container), a filter 56 (which may be a leukoreduction filter), and associated connecting tubing. The pump cassette 48 routes the fluid flow through three tubing loops that extend from the cassette 48, and each loop is uniquely positioned to engage a particular one of the pumps 18-22. The tubing may extend through the cassette 48 or the cassette 48 may have preformed fluid flow paths that direct the fluid flow. The membrane separator 50 employs a membrane-covered rotor within a stationary housing for separating one fluid component (which may be plasma) from another fluid component (which may be the cellular components of whole blood), and is rotated by a magnetic drive unit associated with the mounting station 24.

The modules are individually positioned on the processing device 12. With respect to the fluid module, the fluid container 44 is suspended on a weight scale hanger 38a on the front of the processing device 12, and the associated fluid flow tubing 46 extends from the lower end of the fluid container 44, through the sensor 34, tubing clamp 32a, and to the sterile connection device 30a, where it will eventually be joined with tubing from the processing module.

With reference to the additive solution module (best seen in FIG. 1B), the additive solution container 40 is suspended on weight scale hanger 38b on the side of the processing device 12, and the associated fluid flow tubing 42 extends from the lower end of the additive solution container 40, through the additive fluid tubing clamp 32b, and to the sterile connection device 30b, where it will be joined with tubing from the processing module.

Turning to the processing module, the membrane separator 50 is placed in association with the separator mounting/drive station 24. The pump cassette 48, through which fluid flow is routed for pump control, is mounted at a pumping station adjacent to the pumps 18-22, so that the tubing loops that extend from the cassette 48 are positioned in registration with and preferably for automatic feeding onto one of the particular pumps 18-22. Fluid tubing segment 58 extends from the cassette 48 to the sterile connection device 30b for automatic connection to the tubing 46 associated with the fluid container 44. The fluid tubing segment 58 or its flowpath continues through the cassette 48, forming an external tubing loop for cooperation with the fluid pump 18, which is illustrated as a rotary peristaltic pump, and then continues from the cassette 48 to a fluid inlet 60 of the membrane separator 50.

The membrane separator 50 separates the fluid into first and second fluid components. The second component (which may be plasma, if whole blood is being processed) is directed from the separator 50 into the pre-attached second fluid component container 54, which is suspended on weight scale hanger 38c on the front of the processing device 12. For flowing the second fluid component from the membrane separator 50 into the second fluid component container 54, tubing segment 62 connects the second fluid component container 54 and a second fluid component outlet 64 of the membrane separator 50, and extends through the clamp/sealer/sensor 28a.

The first fluid component (which may be cellular blood components) flows from the membrane separator 50 through a first fluid component exit port 66 of the membrane separator 50 and through a first fluid component tubing segment 68, into the pump cassette 48. The first fluid component tubing segment 68 continues to the cassette 48 and forms an external tubing loop for cooperation with the fluid component pump 20. From the cassette 48, the first fluid component tubing segment 68 continues upwardly and over to the filter 56, which removes a substance (which may be white blood cells) from the first fluid component. From the filter 56, the first fluid component tubing segment 68 extends through clamp/sealer/sensor 28b and into the first fluid component container 52, which is suspended from a weight scale hanger 38d on the side of the processing device 12.

To help preserve the viability of the first fluid component, the additive solution from the additive solution container 40 is added to the first fluid component container 52. Specifically, the additive solution flow tubing 42 is connected, by sterile connection device 30b, to an additive flow tubing segment 70 that is part of the processing module. The tubing segment 70 extends to the cassette 48, and additive solution flows through an external loop cooperating with the additive solution pump 22. Downstream of the pump 22, the additive solution flows into first fluid component flowpath (tubing segment 68 or a preformed flowpath) within the cassette 48, where it mixes with the first fluid component. Thereafter the combined additive solution and first fluid component flows through the first fluid component tubing segment 68 to the filter 56 and into the first fluid component container 52.

A tubing segment 72 extends between the cassette 48 (where it communicates with the first fluid component flowpath) and the first fluid component container 52, generally parallel to the first fluid component tubing segment 68. This segment is filled with fluid from the fluid container 44 and sealed at spaced apart locations by the blood processing personnel to provide a series of blood-filled "segments" that may be later severed for sampling, testing, or cross-matching.

This tubing segment 72 also provides a pathway that allows removal of residual air from the first fluid component container 52 after processing is completed. The pumps may be used to pump residual air from the first fluid component container 52 to the empty fluid container 44 through tubing segment 72 and eventually back to the fluid container 44.

The tubing segment 72 has one additional benefit. It may be used to flow the first fluid component directly into the first fluid component container 52, bypassing the filter 56. This is particularly useful in situations where the first fluid component cannot be filtered. For example, when the filter 56 is provided for removing white blood cells from concentrated red blood cells, it may be the case that the red blood cells cannot be filtered for any of a number of known physiological reasons, such as for donors suffering from sickle-cell anemia. For those, the filter 56 can be bypassed and the second fluid component can still be processed and collected.

As explained above, the disposable fluid circuit 14 is assembled from separate modules in the illustrated embodiment and sterile connection (sometimes called sterile docking) devices 30a and 30b are provided for connecting fluid flow tubing of the different modules. The sterile connection devices 30a and 30b may employ any of several different operating principles.

Figure 1B:
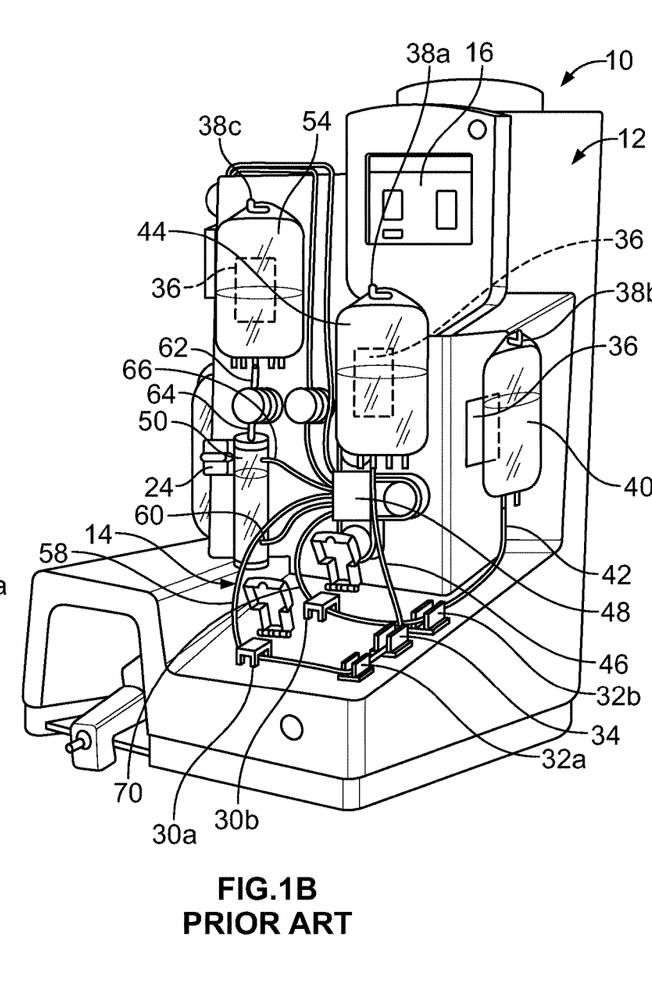
FIG. 1B is a perspective view of the fluid processing system of FIG. 1A, taken from a different angle.

Further, as shown in FIGS. 1A and 1B, the illustrated processing device 12 includes an optical detector 36 associated with and facing each of the containers. Each optical detector 36 is configured to view or read a barcode and/or other information or image on the facing side of the particular container (such as on a label) and to communicate information contained or encoded in the barcode, an image of all or a portion of a label, and/or other information to the device processor and/or to a local or remote data management system for recording as part of a process record, tracking and/or quality control purposes. The information may be communicated in any suitable manner, and the device may be configured to communicate the information via direct wire connection, Internet, LAN, WIFI, Bluetooth, or other suitable communication means. As described above, proper orientation of the container (and, hence, the image to be detected) with respect to the optical detector 36 helps to ensure that the image is detected by the optical detector 36. Approaches for ensuring proper orientation of a container with the associated optical detector 36 will be described herein in greater detail.

B. Containers

Figures 2, 3:
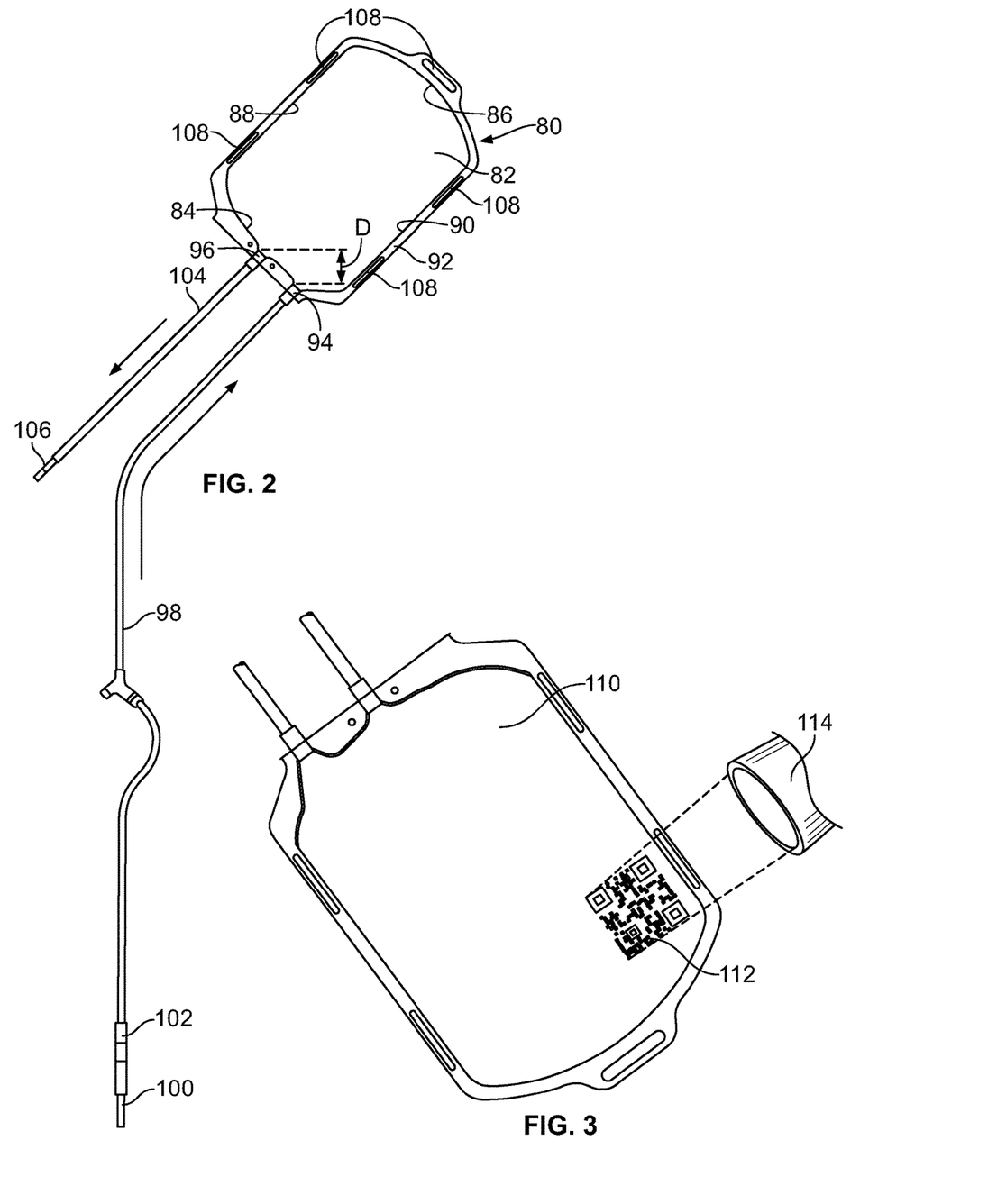
FIG. 2 is a front view of a container of the disposable fluid flow circuit of FIGS. 1A and 1B.
FIG. 3 is a perspective diagrammatic view of a container with a two dimensional barcode, and an optical detector for optically detecting the barcode.

FIG. 2 depicts a single container and tubing set or module. The container 80 is formed from a pair of facing flexible plastic films or sheets 82, which may be made of any suitable heat-sealable material such as, but not limited to, polyvinylchloride. The container 80 has an internal cavity with a first portion or end 84, an opposed second portion or end 86, a first side or lateral portion 88, and an opposed second side or lateral portion 90. The sheets 82 are sealed together, as by radio frequency (RF) or heat seal, along a seal line 92 that extends around the entire periphery of the container 80 and is uninterrupted except for an inlet port 94 and an outlet port 96 located at the first end 84 of the container cavity. The position of the ports 94 and 96 may vary, but in the illustrated embodiment, the inlet port 94 is between the outlet port 96 and the second side 90 of the container 80, and preferably substantially adjacent to the corner or junction between the first end 84 and the second side 90. The outlet port 96 is illustrated as being generally midway between the first and second sides 88 and 90. Alternatively, it should be noted that ports 94 and 96 may be either inlet or outlet ports, depending on intended usage.

The inlet port 94 is connected to inlet flow tubing 98, which extends to a pre-attached access device 100, such as a needle, or to connector, such as a standard luer lock, for connection to an access device 100. The inlet flow tubing 98 may have additional ports or connection sites as desired, such as for pre-donation sampling or the like. It may also include an internal frangible valve 102 that normally blocks flow through the tubing and can be opened by manual manipulation or bending of the tubing.

Outlet fluid flow tubing 104 extends from the outlet port 96 to a sealed distal end 106. The tubing 104 has a length sufficient to extend from the container 80 to a sterile connection device, such as the sterile connection device 30b located on the processing device 12. The length of the tubing 104 may vary depending on the configuration of the device 12, to extend through the illustrated sensor 34 and clamp 32a and to the sterile connection device 30a. In the case of blood processing, the use of outlet tubing separate from the inlet tubing helps prevent introduction of blood clots into a downstream processing module or system if the user fails, at the time of collection, to express any blood remaining in the inlet tubing 98 (also called stripping the blood) into the container 80.

Hanging apertures, shown for purposes of illustration and not limitation as slits 108 (which may vary in number and/or location), are provided in the seal line 92 to allow for suspending the container 80, such as from a weight scale hook 38a-38d as employed in the processing device 12. The slit 108 located in the second end 86 of the container 80 allows the container 80 to be suspended vertically and the slits 108 along the sides 88 and 90 of the container 80 allow it to be suspended so that it hangs in a direction other than vertically, such as horizontally or at an downward angle such as shown in FIG. 2, where the inlet port 94 is slightly lower than the outlet port 96 by a distance D. In the case of whole blood, hanging in this position allows any solids in the collected blood, such as clots, to settle away from the outlet port 96, and helps avoid blocking of the outlet flow tubing 104 by such solids or introduction of such solids into downstream processing system components.

C. Container Images And Detection

FIG. 3 illustrates a particularly efficient arrangement for information transfer and recordation. Shown there is an example of a fluid or fluid component container 110 of the general type, such as the single container 80 of FIG. 2, discussed above. A two-dimensional barcode 112 is located on the container 110, and may contain important information useful in tracking and quality control, and can be scanned or detected by a scanner or optical detector 114 (which may correspond to one of the optical detectors 36 of FIGS. 1A and 1B). Currently, for containers to be used in blood processing, the pertinent regulatory authorities allow information to be placed at particular locations on the container 110. For some types of information, the information is required to be spaced sufficiently far apart or on different sides of the container 110 and cannot be read or optically detected by a single optical detector or scanner in a fixed location of the processing device. An example of this is the manufacturer's part number or catalog number, which may be on the back of the container 110, and the product expiration date, which may be on the bottom right corner of the front of container 110.

A two dimensional barcode has the capability of storing a large amount of information, much more than the typical single dimension or linear barcode. Thus, a two-dimensional barcode may be employed that contains pertinent manufacturer's data in a location on a container or container label that is preferably facing or otherwise visible from a fixed optical detector 114 of the processing device, similar to the optical detectors 36 shown in FIGS. 1A and 1B. A "two-dimensional barcode" is not limited to a particular code format, specification or standard, but it is intended to be a general term, used in accordance with its ordinary meaning, which refers to a two-dimensional representation or matrix, that contains or encodes information based on dark and light spots or areas within the matrix, which matrix is typically but not exclusively square or rectangular, and in contrast to a one-dimensional barcode based on a series of lines and spaces. The stored or encoded information may include, without limitation, any one of the manufacturer's part number or catalog number for the container or module, lot number, expiration date, product code for the blood product to be contained in it, and other such information, alone or in any desired combination. A part number or catalog number may be particularly beneficial to encode, either alone or in combination with a product expiration date. Optionally, in the case of whole blood as a fluid to be processed, the barcode may include any additional manufacturer information required by the United States Consensus Standard for the Uniform Labeling of Blood and Blood Components. This does not preclude the required information from also appearing elsewhere to meet regulatory requirements, but having this information encoded into a single two-dimensional barcode allows a single optical detector 114 to detect all of the information automatically and without user manipulation, so that the information can be retained as part of the stored process record.

Figures 4, 5:
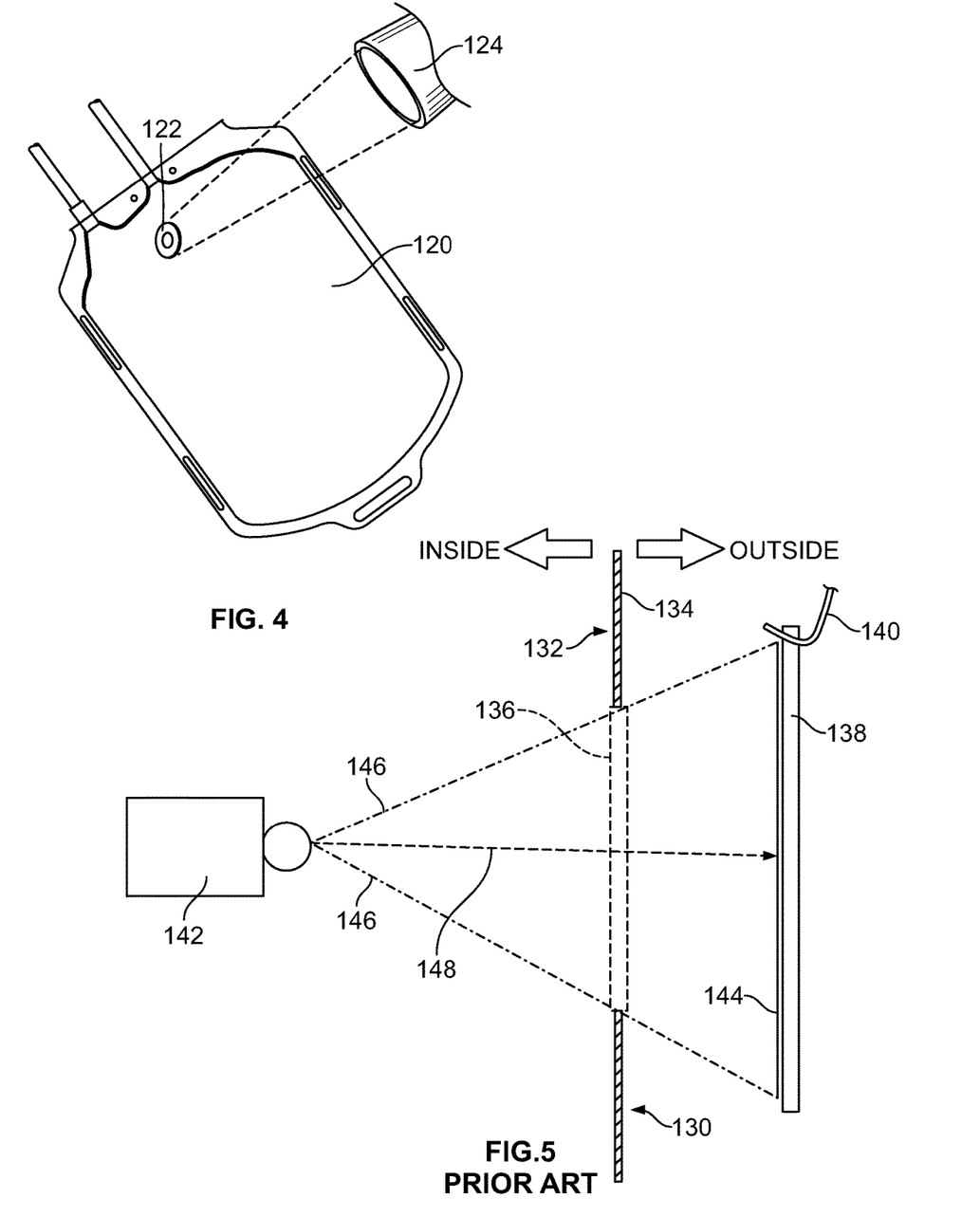
FIG. 4 is a perspective diagrammatic view of a container with a trade logo, and an optical detector for optically detecting the trade logo.
FIG. 5 is a diagrammatic cross-section of a fluid processing device, such as the fluid processing device of FIGS. 1A and 1B, showing positioning of an optical detector in the processing device.

FIG. 4 diagrammatically depicts a fluid or fluid component container 120 bearing a trade logo or identifier 122 of unique design or configuration associated with a particular source that can be detected by an optical detector 124 to determine and authenticate that the disposable is genuine and is what it purports to be—in this case a product of that particular source—in this case, for example, Fenwal, Inc. "Trade logo" as used herein is intended to be general and may include any design and/or combination of numbers or letters or designs that is identified with a particular source of the product. Trade logo may include a registered trademark, but is not limited to such.

More specifically, the processing device employing such a system could include a programmable control processor and onboard data storage, lookup table, or the like (or access to remote data storage) of selected characteristics of such a trade logo on a genuine container, e.g., a genuine blood component container from the source or manufacturer. Such characteristics could be any one or more of numerous aspects including, without limitation, one or more characteristics such as the position coordinates of the logo on the container 120, spacing between certain numbers or letters contained in the logo, font or image size, ratios of sizes of certain aspects such as ratios of different font sizes, density of the image or ink density on certain parts of the logo, logo image resolution, and logo ink material. The detected characteristics of the container 120 in question would be compared to the stored reference characteristics of the logo on a genuine product and, based on the comparison, the controller would determine if the detected and stored characteristics are the same or sufficiently the same for the product in question to be deemed genuine. If not, the controller could generate an alarm or alert condition, such as an audio, visual, or other signal, or even disable operation of the fluid processing device until an operator intervenes.

The optical detector 124 for this application could be separate from the barcode scanner 114 described above or, if practicable, combined into a single optical detector or scan unit, such as optical detector 36 of the processing device 12 of FIGS. 1A and 1B. As with the two-dimensional barcode 112 discussed above, the trade logo 122 is preferably on a surface of the container 120 or a container label facing the processing device when the container 120 is suspended thereon, so that the logo can be scanned automatically without the need for user manipulation.

FIG. 5 diagrammatically shows the positioning of an optical detector in a fluid processing device, such as the optical detectors 36 of the fluid processing device 12 of FIGS. 1A and 1B. As shown in partial view of FIG. 5, the fluid processing device 130 has a housing 132 with a wall or surface 134 and an aperture in the surface 134 forming a window 136. The window 136 is located adjacent to the position where a container 138, such as a fluid or fluid component container, additive solution container, or other container, would hang when suspended from a hanger 140 or other suspension member (e.g., a clamp) of the fluid processing device 130. The window 136 preferably employs glass that is shielded against electromagnetic interference. An optical detector 142 is located within the housing 132, behind the window 136. Similar configurations may be seen in FIGS. 1A and 1B, where optical detectors 36 are located on the fluid processing device 12 behind and facing each container 40, 44, 52, and 54.

The optical detector 142 may be of any suitable design or employ any suitable technology for scanning, imaging, or otherwise detecting images, such as ones of the type described herein. For example, the optical detector 142 may employ a laser, camera, CCD scanner, or other suitable imaging or scanning device or technology.

As noted above, the optical detector 142 is preferably mounted within the housing 132 for protection and positioned to optically view or scan an image on the container 138 (which may include an image on a label 144 secured to the container 138) through the window 136. The optical detector 142 is positioned so that it scans or images a particular surface area of the container 138 (which may be a portion of the label 144). More specifically, the optical detector 142 is preferably positioned to detect an image printed on the container 138 or on a label 144 on the surface of the container 138 facing the window 136. As described above, exemplary images include a barcode (e.g., the two-dimensional barcode discussed earlier) and/or a trade logo.

In the medical field in general and in the field of blood collection and processing in particular, aspects of the container and container label may be subject to certain requirements of regulatory or standard-setting bodies. Typically, labels on containers for blood or blood components are rectangular and have a size of about 4 inches (102 mm) in width and 4 inches (102 mm) in length. ISO3826 standard shows a label for a blood component container having a label size of 105 mm×105 mm (4.1 inches×4.1 inches). The labels may also need to comply with other standards such as ISBT-128, ST-005, which requires the container to carry a Base Label of 100+/−2 mm×106+/−2 mm (3.9 inches×4.2 inches). Thus, these labels are generally within a space of 4+/−0.25 inches×4+/−0.25 inches. For purposes of this description the above labels, even though slightly larger or smaller, are deemed to be substantially 4 inches×4 inches.

To better ensure that the optical detector 142 detects an image printed on the label 144 (if present) or on the container 138, the optical detector 142 may be configured to image the entire or substantially the entire label 144 or a portion of the container 138 of that size and configuration. To achieve this, the optical detector 142 is particularly positioned within the housing 132. In the illustrated embodiment, the optical detector 142 has a field of view 146 (which can have vertical and horizontal aspects—only vertical being shown in FIG. 5) and focal length or distance 148. To image the desired surface area of the container 138 of about 4 inches×4 inches, an optical detector 142 having a vertical field of view of about 30-40 degrees and an equal or larger horizontal field of view, could be positioned about 6-8 inches (about 15-20 cm) from the surface of a suspended container 138. This configuration may vary based on the size of the particular area to be imaged and the particular optical detector employed, without departing from the scope of the present disclosure.

Figure 6:
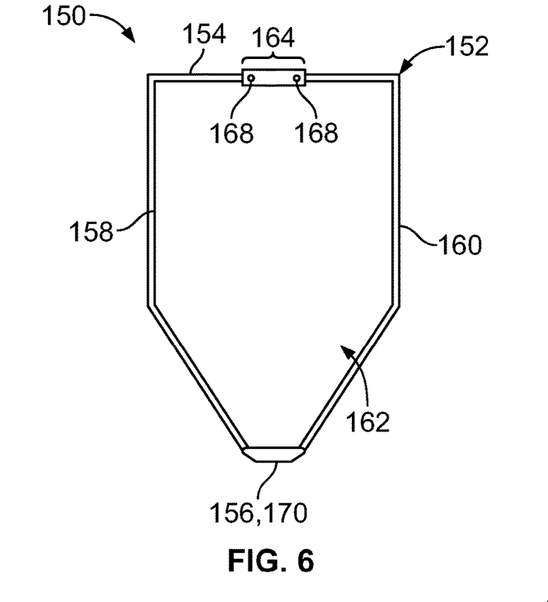
FIG. 6 is a front elevational view of an embodiment of a fixture for mounting a container with respect to an optical detector, according to an aspect of the present disclosure.
Figure 7:
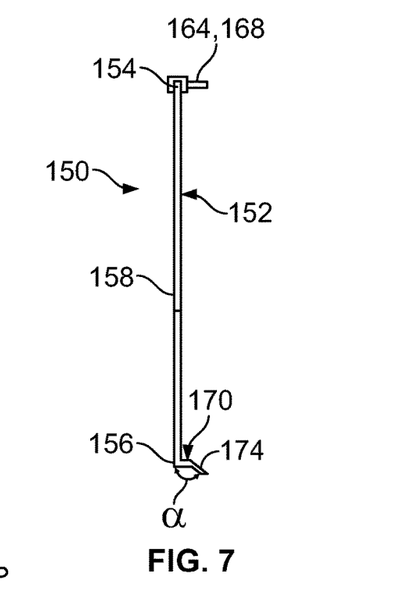
FIG. 7 is a side elevational view of the fixture of FIG. 6.

FIG. 5 illustrates a preferred orientation of the container 138 with respect to the surface 134 and the optical detector 142 but, as described above, a conventional hanger 140 may be ineffective in properly orienting the container 138, particularly when the container 138 is empty. FIGS. 6 and 7 illustrate a fixture 150 that may be provided to ensure proper, fixed orientation of the container 138. The fixture 150 is provided with a frame 152 having a first portion 154 and a second portion 156. One of the first and second portions 154 and 156 is positioned above the other one of the first and second portions 154 and 156. Thus, while FIGS. 6 and 7 show the first portion 154 positioned above the second portion 156, it should be understood that the second portion 156 may instead be positioned above the first portion 154.

The first and second portions 154 and 156 (which may comprise opposing ends of the frame 152) are joined by lateral portions 158 and 160 (which may comprise opposing edges of the frame 152), with the frame 152 defining an opening 162 between the first and second portions 154 and 156 and between the lateral portions 158 and 160. The frame 152 is shown in FIG. 7 as being generally planar, which may be advantageous for constraining an associated container 138 into a fixed, generally planar, and substantially parallel orientation with respect to an associated surface 134 of a processing device 130, but it should be understood that the frame 152 may also be non-planar without departing from the present disclosure. The frame 152 is preferably formed of a substantially rigid material (e.g., a metallic or plastic material), such that it retains its configuration when a container 138 is mounted thereto.

Figure 8:
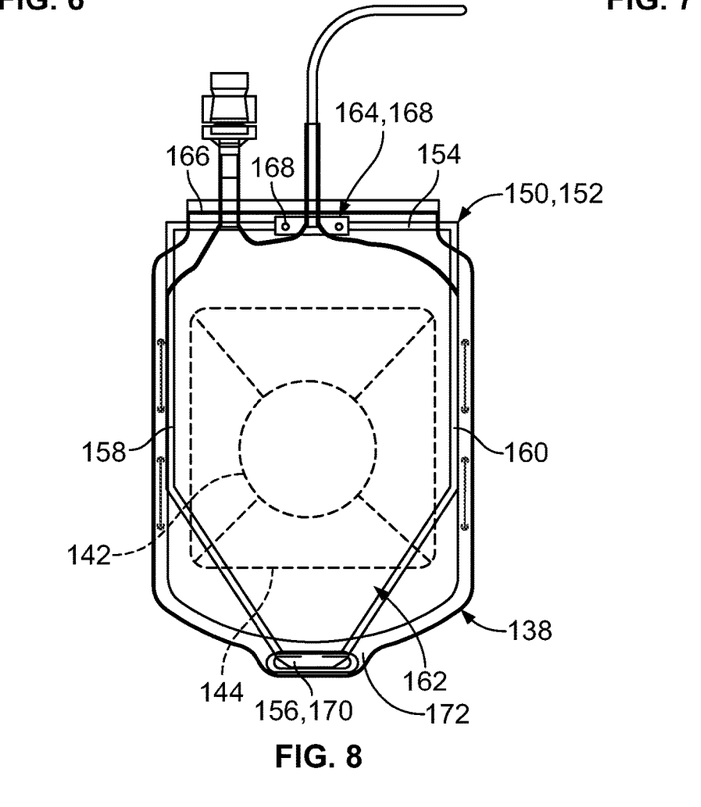
FIG. 8 is a front elevational view of the fixture of FIG. 6, showing a container mounted to the fixture and oriented in alignment with an optical detector.

A first support 164 extends from the first portion 154 of the frame 152 to engage a first portion or end 166 of the container 138 (FIG. 8). In the illustrated embodiment, the first support 164 comprises a plurality of substantially identical extensions 168, which may be particularly well-suited for receipt by a pair of slits or openings defined in the first portion or end 166 of the associated container 138, as in the configurations of FIGS. 2-4. However, it should be understood that the particular configuration of the first support may vary in order to conform to the configuration of the associated container.

A second support 170 extends from the second portion 156 of the frame 152 to engage a second portion or end 172 of the container 138. In the illustrated embodiment, the second support 170 comprises a single extension that is elongated in a lateral direction, which may be particularly well-suited for receipt by an elongated slit or opening defined in the second portion 172 of the associated container 138, as in the configurations of FIGS. 2-4. However, it should be understood that the particular configuration of the second support may vary in order to conform to the configuration of the associated container. It should also be understood that the illustrated support configurations may be reversed, with a second support comprising a plurality of extensions and the first support comprising a single (optionally laterally elongated) extension. This may be advantageous if the orientation of the container 138 is to be inverted with respect to the orientation shown in FIG. 8.

When securing a container 138 to the fixture 150, the first portion 166 of the container 138 may be associated to the first support 164 before the second portion 172 is associated to the second support 170. Alternatively, the second portion 172 of the container 138 may be associated to the second support 170 before the first portion 166 is associated to the first support 164. In yet another embodiment, the first and second portions 166 and 172 of the container 138 may be substantially simultaneously associated to the first and second supports 164 and 170, respectively.

The fixture 150 may be configured to be entirely separate from the fluid processing device 130 and self-supporting (e.g., using a base, which is not illustrated), particularly when the fluid processing device 130 is not configured to weigh a container 138 mounted to the fixture 150. On the other hand, if the fluid processing device 130 is configured to weigh a container 138 mounted to the fixture 150, it may be advantageous for the fixture 150 to be configured to be supported by the fluid processing device 130. For example, in one embodiment, the fixture 150 may be suitable for being hung from or supported by a hanger 38a-38d of the type shown in FIGS. 1A and 1B or a hanger 140 of the type shown in FIG. 5. Thus, rather than a container being directly hung on a hanger in front of an optical detector, it is mounted to the fixture 150, which is hung from the hanger to properly position an image on the container (or on a label of the container, which is considered to be an image on the container) in alignment with the optical detector. FIG. 8 illustrates the position of an optical detector 142 with respect to a container 138 and label 144 mounted on the fixture 150, which is hung from a hanger (not illustrated) of the fluid processing device 130. As can be seen, the opening 162 defined between the first and second supports 164 and 170 prevents the fixture 150 from blocking the field of vision of the optical detector 142. If the optical detector 142 is associated with a window (as in the embodiment of FIG. 5), it may be advantageous for the opening 162 to be configured such that the fixture 150 does not block any portion of the window.

Not illustrated in FIG. 8 is an image, which is positioned between the first and second portions 166 and 172 of the container 138, but the first and second supports 164 and 170 cooperate to retain the container 138 (even if empty) in proper position with respect to the optical detector 142, such that the optical detector 142 will be capable of optically detecting the image. The weight of the fixture 150 may be considered by a weight scale associated with the hanger to prevent the presence of the fixture 150 from giving an improper reading of the weight of the container 138.

More particularly, rather than relying upon a single support and gravity to retain the container 138 in proper position with respect to the optical detector 142 (as in FIG. 5), the pair of supports prevents the container 138 from moving away from the proper orientation, even if it is empty. The separation between the first and second supports 164 and 170 may be at least generally or substantially equal to the spacing between mating features (e.g., holes or slits) associated with the first and second portions 166 and 172 of the associated container 138. In some embodiments, it may be preferred for the spacing between the first and second supports 164 and 170 to be (perhaps only nominally) greater than the spacing between the mating features of the container 138, particularly if the container 138 is already filled with fluid and formed of a flexible material (to force the container to be stretched or deformed to be mounted to the fixture 150). In other embodiments, it may be preferred for the spacing between the first and second supports 164 and 170 to be (perhaps only nominally) smaller than the spacing between the mating features for ease of mounting the container 138 to the fixture 150, without being so much smaller so as to allow the container 138 to deform to an improper orientation.

In the illustrated embodiment, the second support 170 includes a portion 174 extending away from the first support 164, at a downward angle α (FIG. 7), which may be an approximately 45° angle in one embodiment. This may be advantageous, rather than both of the supports 164 and 170 extending orthogonally from the frame 152, as the angled portion 174 may better prevent a container from being unintentionally disengaged from the fixture 150. In other embodiments, the first support 164, rather than the second support 170, may include such a portion that extends away from the other support. In yet another embodiment, one or both of the supports 164 and 170 may include a deformable portion, which is movable from a first configuration to a second configuration, with the first configuration allowing for the mating portion of a container to be readily associated to the support and the second configuration locking that portion of the container to the support or otherwise making it more difficult to remove the container from the support. For example, if a first or second portion of the container is not provided with a hole or slit to receive an associated support, the support may instead be configured as a clip or clamp that may be opened to insert a portion of the container and then closed to retain the container. In yet another embodiment, a support may include a weak adhesive that holds the associated portion of the container in place, while allowing the container to be separated from the fixture following use.

Figure 9:
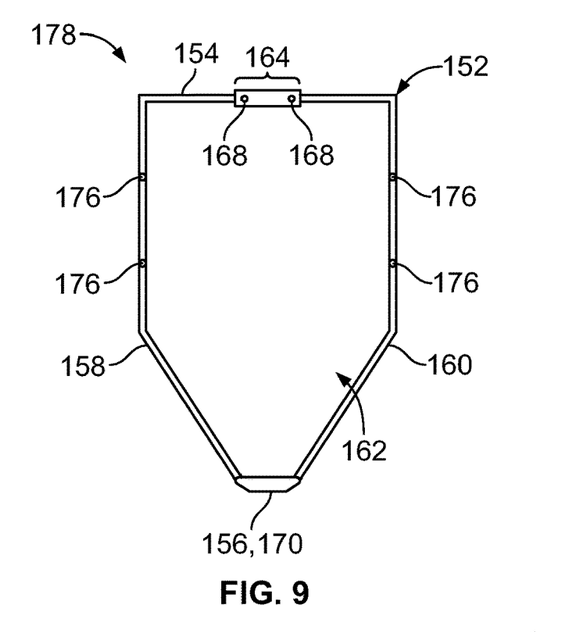
FIG. 9 is a front elevational view of another embodiment of a fixture for mounting a container with respect to an optical detector.
Figure 10:
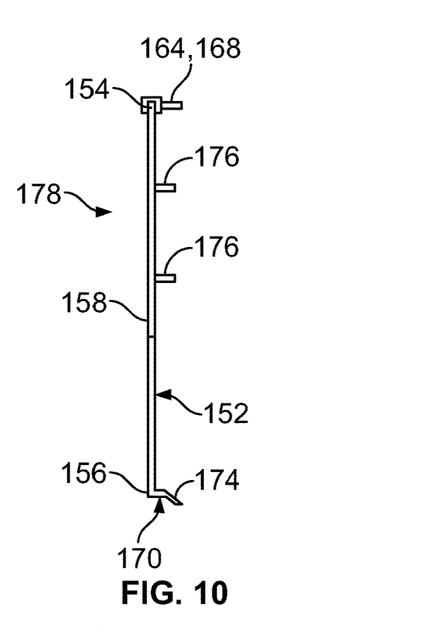
FIG. 10 is a side elevational view of the fixture of FIG. 9.

In another embodiment, which is shown in FIGS. 9 and 10, one or both of the lateral portions 158 and 160 of the frame 152 may include a lateral support 176, which is configured to engage a corresponding lateral portion of a container to be mounted to the fixture 178. For example, each of the lateral portions of the containers of FIGS. 2-4 include a pair of slits 108, in which case each lateral portion 158, 160 of the frame 152 may include a lateral support 176 comprising a pair of extensions, with each extension being received by a different one of the slits 108. Any lateral supports may be configured according to the configurations described previously with respect to the first and second supports 164 and 170. Additionally, rather than the lateral supports 176 being provided in addition to the first and second supports 164 and 170, it is also within the scope of the present disclosure for the fixture 178 to be provided with only lateral supports 176, such that the lateral supports 176 of the opposing lateral portions 158 and 160 of the frame 152 alone cooperate to ensure that the container is properly positioned with respect to an associated optical detector.

Figure 11:
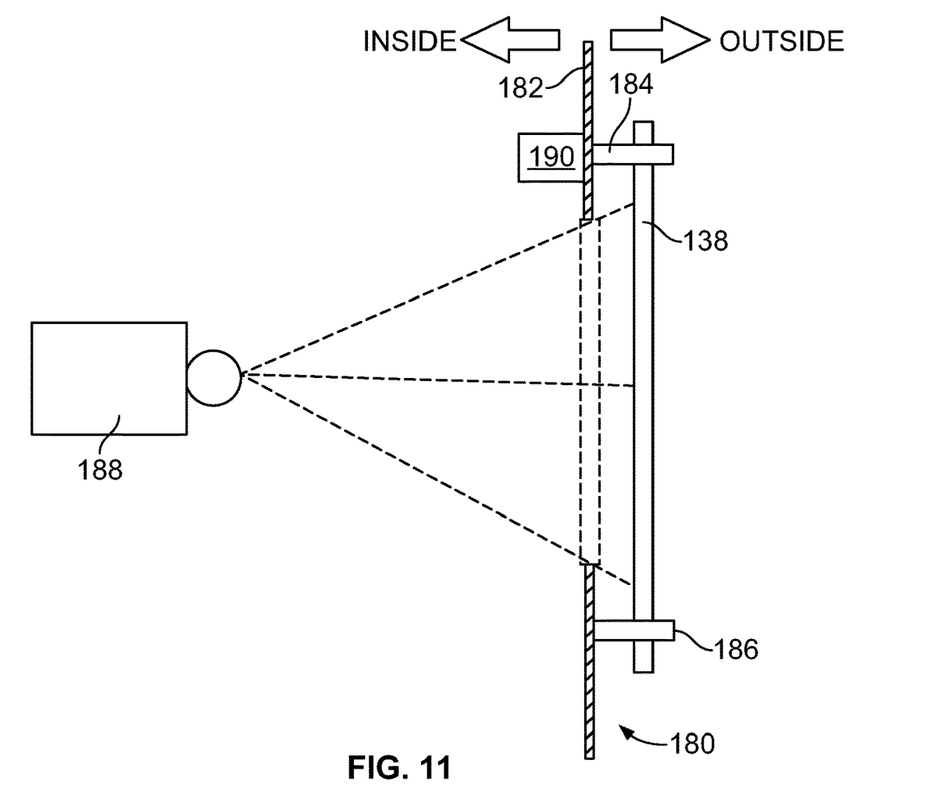
FIG. 11 is a diagrammatic cross-section of a modified fluid processing device, showing a container positioned with respect to an optical detector of the processing device.

Alternatively, rather than providing a separate fixture to promote proper orientation of a container with respect to the optical detector of a fluid processing device, the fluid processing device may be reconfigured to perform a similar function. For example, FIG. 11 shows a fluid processing device 180 that is a variation of the device 130 of FIG. 5. Whereas the device 130 of FIG. 5 relies upon a single hanger 140 and gravity to properly orient a container 138, the fluid processing device 180 of FIG. 11 includes a surface 182 from which a first support 184 and a second support 186 extend. One of the supports is positioned above an optical detector 188 of the device 180, while the other support is positioned below the optical detector 188. As with a separately provided fixture 150, the supports 184 and 186 may be associated to corresponding portions of the container 138 sequentially or substantially simultaneously.

Whichever support is positioned above the optical detector 188 (illustrated in FIG. 11 as the first support 184) may be similarly configured to a hanger 38*a*-38*d* of the type shown in FIGS. 1A and 1B, which may include being a portion or component of a weight scale 190. In one embodiment, the lower support (illustrated in FIG. 11 as the second support 186) may be removably associated with the surface 182, such as being configured as a peg or post that is partially received within a cavity defined in the surface 182. This may be advantageous in allowing differently configured supports to be employed, which may be necessary if differently sized and/or configured containers may be paired with the optical detector 188.

The supports 184 and 186 are shown generically in FIG. 11, but may be variously configured without departing from the scope of the present disclosure. For example, the supports 184 and 186 may be configured according to the preceding description of the first and second supports 164 and 170 of a fixture 150 that is separately provided from an associated fluid processing device. Furthermore, as in the fixture 178 of FIGS. 9 and 10, the fluid processing device 180 may include at least one lateral support extending from the surface 182 and positioned laterally of the optical detector 188. If a lateral support is provided on one side of the optical detector 188, it may be advantageous to provide at least one lateral support on the other side of the optical detector 188, such that the lateral supports may cooperate to hold a container 138 taut and in proper position with respect to the optical detector 188. Additionally, rather than the lateral supports supplementing the first and second supports 184 and 186, it is also within the scope of the present disclosure for the surface 182 of the fluid processing device 180 to be provided with only lateral supports, while omitting the first and second supports 184 and 186.

The embodiment of FIG. 11 may be advantageous compared to the use of a separate fixture 150, as there is no concern about the fixture 150 being lost or misplaced. However, if the upper support is incorporated into a weight scale 190, care must be taken to ensure that the retaining force applied to the container 138 by the lower support does not affect the readings of the weight scale 190. Thus, it may be advantageous for the supports 184 and 186 to be more closely positioned than the supports 164 and 170 of a separate fixture 150 for a given container 138 to avoid skewing the readings of the weight scale 190.

Figure 12:
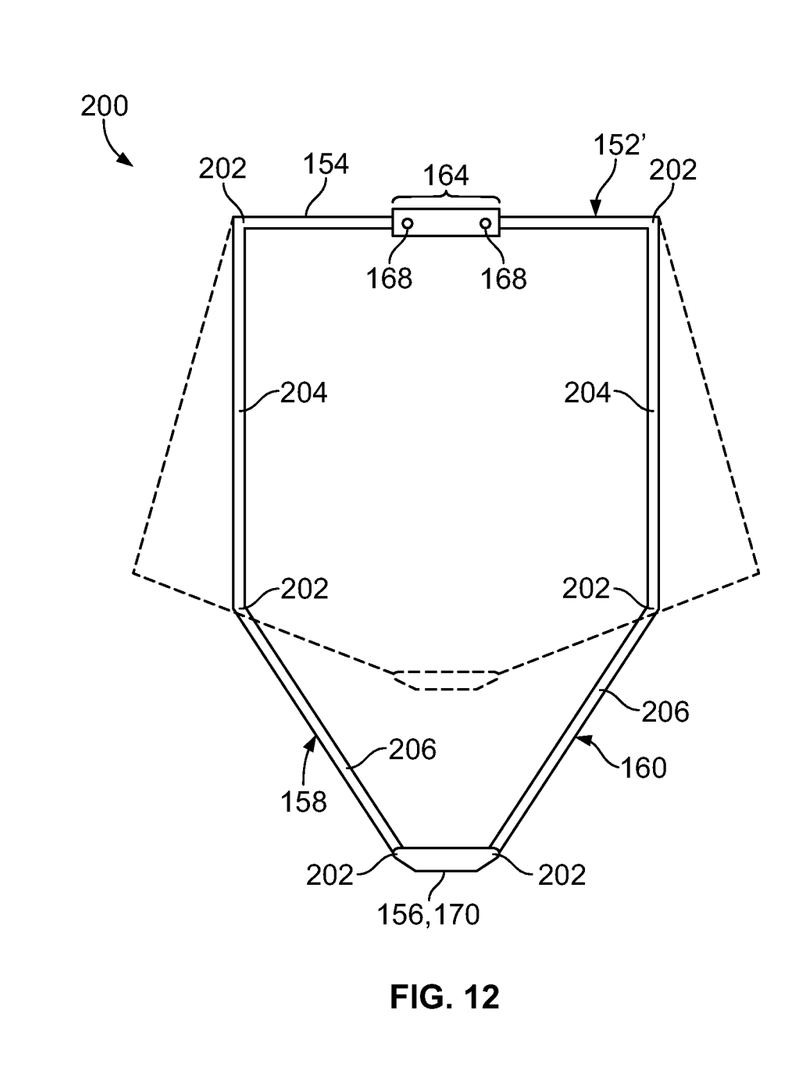
FIG. 12 is a front elevational view of an adjustable fixture, showing in broken lines an alternative configuration of the fixture.
Figure 13:
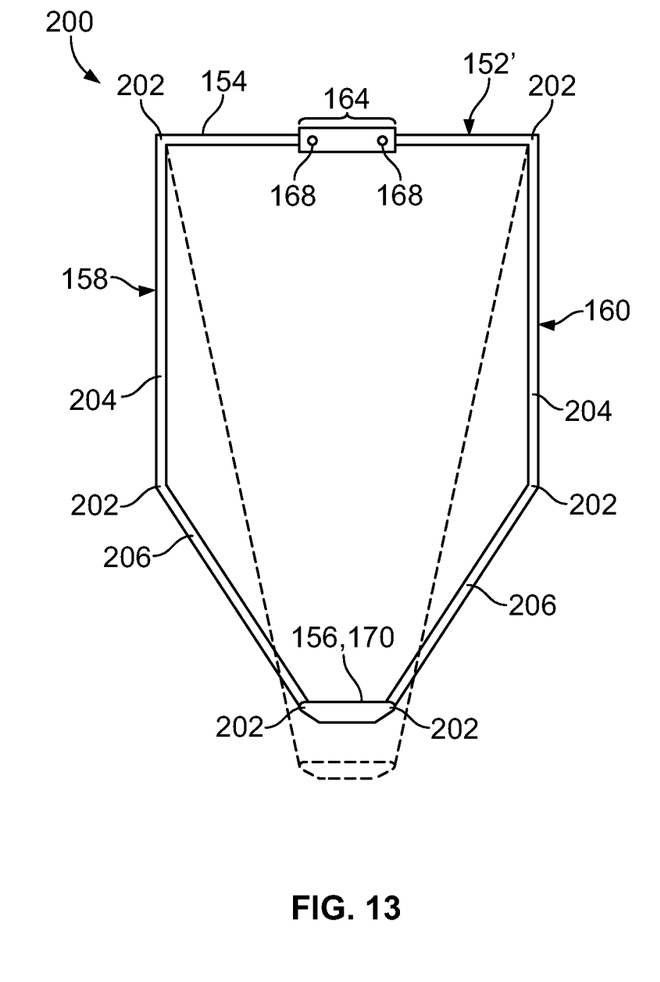
FIG. 13 is a front elevation view of the adjustable fixture of FIG. 12, showing in broken lines another alternative configuration of the fixture.

FIGS. 12 and 13 illustrate a variation of the fixture 150 of FIG. 6. It should be understood that the features of the fixture 200 of FIGS. 12 and 13 are not limited to incorporation into a fixture of the type illustrated in FIG. 6, but may be incorporated into any separately provided fixture, such as the fixture 178 of FIG. 9.

The fixture 200 of FIGS. 12 and 13 may be configured according to the foregoing description of the fixture 150 of FIG. 6 (with similar components of the two fixtures 150 and 200 having identical labels), but with the ability to be adjusted to assume a plurality of configurations, rather than being limited to one configuration. In particular, the fixture 200 of FIGS. 12 and 13 includes a plurality of hinges or points of articulation 202, which allow it to move from an initial configuration (shown in FIGS. 12 and 13 in solid lines) to any of a number of alternative configurations (shown in FIGS. 12 and 13 in broken lines). In the embodiment of FIGS. 12 and 13, the frame 152' includes six hinges 202, with one hinge 202 located at each end of the first and second portions 154 and 156 and one hinge 202 located at the junctions of the arms or sections 204 and 206 of each lateral portion 158, 160. It should be understood that the fixture 200 is not limited to a particular number of hinges 202 and/or a particular location for any of the hinges 202, but rather the illustrated embodiment is merely exemplary.

The hinges 202, which may include springs or be otherwise configured without departing from the scope of the present disclosure, allow for the angle or orientation of a region of the frame 152' to be adjusted with respect to an adjacent region of the frame 152'. By the provision of such hinges 202, the distance between the first support 164 and the second support 170 may be adjusted, with FIG. 12 showing an alternative configuration having a smaller distance between the first and second supports 164 and 170 (due to a reduced angle between the arms 204 and 206 of each lateral portion 158, 160) and with FIG. 13 showing an alternative configuration having a greater distance between the first and second supports 164 and 170 (due to an increased angle between the arms 204 and 206 of each lateral portion 158, 160). By allowing for the fixture 200 to be reconfigured to adjust the distance between the first and second supports 164 and 170, a single fixture may be used with differently sized containers (i.e., containers having different lengths between their first and second portions or ends).

It should be understood that the use of hinges 202 is not the only way to allow for adjustment of the distance between the first and second supports 164 and 170. For example, rather than (or in addition to) providing hinges 202, the lateral portions 158 and 160 may have an adjustable length (e.g., by providing parallel upper arms 204 that are telescopic). Thus, rather than varying the distance between the first and second supports 164 and 170 by adjusting the angle between the arms 204 and 206 of the lateral portions 158 and 160, the distance between the first and second supports 164 and 170 may be adjusted by increasing or decreasing the length of the upper arms 204. Other approaches to configuring a fixture so as to allow for adjustment of the distance between its first and second supports may also be employed without departing from the scope of the present disclosure.

Aspects

Aspect 1. A fixture for mounting a container, comprising: a frame; a first support extending from a first portion of the frame and configured to engage a first portion of a container; and a second support extending from a second portion of the frame positioned above or below the first portion of the frame, the second support being configured to engage a second portion of the container, wherein the first and second supports are configured to cooperate to restrain the container in a fixed orientation.

Aspect 2. The fixture of Aspect 1, wherein an opening is defined between the first and second portions of the frame.

Aspect 3. The fixture of any one of Aspects 1-2, wherein the frame is generally planar.

Aspect 4. The fixture of any one of Aspects 1-3, wherein the first and second supports are differently configured.

Aspect 5. The fixture of any one of Aspects 1-4, wherein one of the first and second supports comprises a plurality of extensions.

Aspect 6. The fixture of Aspect 5, wherein the extensions are substantially identical.

Aspect 7. The fixture of any one of Aspects 1-6, wherein one of the first and second supports is elongated in a lateral direction.

Aspect 8. The fixture of any one of Aspects 1-7, wherein at least a portion of one of the first and second supports extends away from the other one of the first and second supports.

Aspect 9. The fixture of any one of Aspects 1-8, further comprising at least one lateral support extending from a lateral portion of the frame and configured to engage a lateral portion of the container.

Aspect 10. The fixture of any one of Aspects 1-9, wherein the first and second supports are configured to restrain the container in an at least generally planar orientation.

Aspect 11. The fixture of any one of the preceding Aspects, wherein a distance between the first and second supports is adjustable.

Aspect 12. A fluid processing device, comprising: a surface; an optical detector associated with the surface; a first support extending from the surface; and a second support extending from the surface, wherein one of the first and second supports is positioned above the optical detector, the other one of the first and second supports is positioned below the optical detector, the first support is configured to engage a first portion of a container including an image positioned between the first portion and a second portion of the container, the second support is configured to engage the second portion of the container, and the first and second supports are configured to cooperate to restrain the container in a fixed orientation with respect to the optical detector.

Aspect 13. The fluid processing device of Aspect 12, wherein said one of the first and second supports positioned above the optical detector comprises a portion of a weight scale.

Aspect 14. The fluid processing device of any one of Aspects 12-13, wherein the first and second supports are differently configured.

Aspect 15. The fluid processing device of any one of Aspects 12-14, wherein one of the first and second supports comprises a plurality of extensions.

Aspect 16. The fluid processing device of Aspect 15, wherein the extensions are substantially identical.

Aspect 17. The fluid processing device of any one of Aspects 12-16, wherein one of the first and second supports is elongated in a lateral direction.

Aspect 18. The fluid processing device of any one of Aspects 12-17, wherein at least a portion of one of the first and second supports extends away from the other one of the first and second supports.

Aspect 19. The fluid processing device of any one of Aspects 12-18, further comprising at least one lateral support extending from the surface, positioned laterally of the optical detector, and configured to engage a lateral portion of the container.

Aspect 20. The fluid processing device of any one of Aspects 12-19, wherein the first and second supports are configured to restrain the container in an orientation that is at least generally parallel to the surface, with the image in at least general alignment with the optical detector.

Aspect 21. A method of mounting a container to a fluid processing device of the type including an optical detector associated with a surface of the fluid processing device, the method comprising: providing a container including a first portion, a second portion, and an image positioned between the first and second portions; associating the first portion of the container to a first support extending from the surface; and associating the second portion of the container to a second support extending from the surface, wherein one of the first and second supports is positioned above the optical detector, the other one the first and second supports is positioned below the optical detector, and the first and second supports cooperate to restrain the container in a fixed orientation with respect to the optical detector, with the image in at least general alignment with the optical detector.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fixture for mounting a container, comprising:
   a frame;
   a first support extending from a first portion of the frame and configured to engage a first portion of a container; and
   a second support extending from a second portion of the frame positioned above or below the first portion of the frame, the second support being configured to engage a second portion of the container, wherein the first and second supports are configured to cooperate to restrain the container in a fixed orientation.

2. The fixture of claim 1, wherein an opening is defined between the first and second portions of the frame.

3. The fixture of claim 1, wherein the frame is generally planar.

4. The fixture of claim 1, wherein the first and second supports are differently configured.

5. The fixture of claim 1, wherein one of the first and second supports comprises a plurality of extensions.

6. The fixture of claim 5, wherein the extensions are substantially identical.

7. The fixture of claim 1, wherein one of the first and second supports is elongated in a lateral direction.

8. The fixture of claim 1, wherein at least a portion of one of the first and second supports extends away from the other one of the first and second supports.

9. The fixture of claim 1, further comprising at least one lateral support extending from a lateral portion of the frame and configured to engage a lateral portion of the container.

10. The fixture of claim 1, wherein the first and second supports are configured to restrain the container in an at least generally planar orientation.

11. The fixture of claim 1, wherein a distance between the first and second supports is adjustable.

12. A fluid processing device, comprising:
    a surface;
    an optical detector associated with the surface; and
    first and second supports extending from the surface, wherein
    one of the first and second supports is positioned above the optical detector,
    the other one of the first and second supports is positioned below the optical detector,
    the first support is configured to engage a first portion of a container including an image positioned between the first portion and a second portion of the container,
    the second support is configured to engage the second portion of the container, and the first and second supports are configured to cooperate to restrain the container in a fixed orientation with respect to the optical detector.

13. The fluid processing device of claim 12, wherein said one of the first and second supports positioned above the optical detector comprises a portion of a weight scale.

14. The fluid processing device of claim 12, wherein the first and second supports are differently configured.

15. The fluid processing device of claim 12, wherein one of the first and second supports comprises a plurality of extensions.

16. The fluid processing device of claim 15, wherein the extensions are substantially identical.

17. The fluid processing device of claim 12, wherein one of the first and second supports is elongated in a lateral direction.

18. The fluid processing device of claim 12, wherein at least a portion of one of the first and second supports extends away from the other one of the first and second supports.

19. The fluid processing device of claim 12, further comprising at least one lateral support extending from the surface, positioned laterally of the optical detector, and configured to engage a lateral portion of the container.

20. The fluid processing device of claim 12, wherein the first and second supports are configured to restrain the container in an orientation that is at least generally parallel to the surface, with the image in at least general alignment with the optical detector.

21. A method of mounting a container to a fluid processing device of the type including an optical detector associated with a surface of the fluid processing device, the method comprising:
providing a container including a first portion, a second portion, and an image positioned between the first and second portions;
associating the first portion of the container to a first support extending from the surface; and
associating the second portion of the container to a second support extending from the surface, wherein
one of the first and second supports is positioned above the optical detector,
the other one of the first and second supports is positioned below the optical detector, and
the first and second supports cooperate to restrain the container in a fixed orientation with respect to the optical detector, with the image in at least general alignment with the optical detector.

* * * * *